United States Patent
Drury

(10) Patent No.: US 6,613,347 B2
(45) Date of Patent: Sep. 2, 2003

(54) PVA SPONGE WITH LOW DUROMETER SKIN SILICONE

(75) Inventor: Thomas J. Drury, Tolland, CT (US)

(73) Assignee: Tolland Development Company, LLC, Willimantic, CT (US)

( * ) Notice: Subject to any disclaimer, the term of this patent is extended or adjusted under 35 U.S.C. 154(b) by 24 days.

(21) Appl. No.: 09/788,347

(22) Filed: Feb. 21, 2001

(65) Prior Publication Data

US 2002/0114826 A1 Aug. 22, 2002

(51) Int. Cl.[7] ............ A61K 9/00; A61K 9/70; A61L 15/00; A61F 13/00
(52) U.S. Cl. ........... 424/443; 424/400; 424/445; 424/449; 427/2.1; 427/393.5; 427/430.1
(58) Field of Search ............... 424/443, 445, 424/449, 400; 427/430.1, 2.1, 393.5

(56) References Cited

U.S. PATENT DOCUMENTS

| | | |
|---|---|---|
| 4,098,728 A | 7/1978 | Rosenblatt |
| 5,071,648 A | 12/1991 | Rosenblatt |
| 5,085,781 A | 2/1992 | Tsuru et al. |
| 5,133,972 A * | 7/1992 | Ferrini et al. ......... 424/449 |
| 5,370,656 A | 12/1994 | Shevel |
| 5,447,505 A | 9/1995 | Valentine et al. |
| 5,466,231 A * | 11/1995 | Cercone et al. ......... 604/369 |
| 5,554,659 A | 9/1996 | Rosenblatt |
| 5,556,391 A | 9/1996 | Cercone et al. |
| 5,744,150 A | 4/1998 | Cercone |
| 5,810,755 A | 9/1998 | LeVeen et al. |
| 5,811,471 A | 9/1998 | Shanbrom |
| 5,928,665 A | 7/1999 | Cercone |

\* cited by examiner

Primary Examiner—Thurman K. Page
Assistant Examiner—Humera N. Sheikh
(74) Attorney, Agent, or Firm—John S. Hale; Gipple & Hale

(57) ABSTRACT

The present invention is directed toward a polyvinyl acetal sponge with a smooth outer low durometer silicone skin having less porosity then the foam center. The PVA sponge is washed free of formaldehyde, dried and hydrated and a thin coating of less than 1 mm low durometer silicone is applied to the surface of the sponge and heated at a low temperature ranging from 100° F. and 150° F. over 8 to 16 hours to cure the silicone skin bonding it to the sponge increasing the tear strength of the skin while preserving elasticity. The composite wound dressing allows moisture adsorption through the skin into the PVA sponge body but presents an outer surface precluding wound growth into the sponge material.

28 Claims, 1 Drawing Sheet

PVA SPONGE WITH LOW DUROMETER SKIN SILICONE

FIELD OF THE INVENTION

The present invention relates generally to a wound care dressing and more specifically relates to a wound care sponge constructed of a polyvinyl acetal composition with an outer low durometer silicone skin ranging from 1–4 mils in thickness.

BACKGROUND OF THE INVENTION

There are a number of major problems encountered in present day wound dressings. Such wound dressings are primarily of the cellulose type and the sponge type. Cellulose dressings have probably have been used in some form since the beginning of recorded history and are basically constructed of cellulose materials such as rayon and cotton. These wound dressings leave Tinting fibers, allow bacterial growth adjacent the wound and allow wound growth extension into the fibers of the dressing. Removal of the dressing also causes tearing of the wound when the dressing is removed and can leave fibrous fragments in the wound. Because of the fiber spacing in such dressings they also do not present a barrier against direct exposure to air and organisms carried in the air.

Advances in the development of synthetic polymers have produced numerous changes in wound care dressings resulting in polymeric foams, polymeric foams, particulate and fibrous polymers, hydrogels and hydrocolloids. These developments have resulted in sponge type dressings being widely used but unfortunately these dressings also suffer from wound growth into the cells of the sponges, lack of absorption and wound tearing problems which occur when the dressings are removed.

A number of sponge type dressings and medical devices have been constructed of PVA material. These products have a significant percent of their alcohol functions acetalized and are open celled, highly water absorbent porous flexible material that wick aqueous solutions quickly. They have high tensile strength, good elongation and excellent resistance to most chemicals and are white in color.

U.S. Pat. No. 4,098,728 issued Jul. 4, 1978 discloses the use of polyvinyl acetal material having a fast wicking and high liquid holding capacity for medical usage.

U.S. Pat. No. 5,071,648, issued on Dec. 10, 1991 discloses a polyvinyl acetal material with a complex of iodine which forms a sponge releasing controlled amounts of iodine sufficient to kill germ cells with minimum toxicity to the surrounding tissue. Likewise, U.S. Pat. No. 5,744,150 issued on Apr. 28, 1998 and U.S. Pat. No. 5,928,665 issued Jul. 27, 1999 disclose a method for producing an antimicrobial iodine polyvinyl acetal sponge which is soaked in a aqueous bath of 20% to 70% triethylene glycol. The resultant product is a wound dressing including an iodine complexed polyvinyl acetal sponge material in which alkylene glycol is applied to the surface of the sponge to soften the sponge and impart a yellow-gold coloration onto the outer surface of the sponge indicating the activation of the antimicrobial elements complexed in the sponge material. U.S. Pat. No. 5,810,755 issued Sep. 22, 1998 discloses a medicated wound dressing with a open cell foam polymeric compound of polyvinyl alcohol complexed with elemental iodine.

U.S. Pat. No. 5,554,659 issued Sep. 10, 1996 and U.S. Pat. No. 5,556,391 issued Sep. 17, 1996 are directed toward a molded porous polyvinyl alcohol sponge including an outer skin having an average pore size smaller than the interior portion of the product capable of absorbing and passing water to the interior portions of the sponge.

U.S. Pat. No. 5,811,471, issued Sep. 22, 1998 discloses a polyvinyl acetal polymer sponge which has a germicidal disinfectant dye bound thereto which is used as a tampon while U.S. Pat. No. 5,447,505 issued Sep. 5, 1995 discloses the use of polyvinyl acetal sponge a surgical dressing. Polyvinyl acetal is already used in the prior art for nasal packings and other surgical packings.

Another article in the prior art as shown in U.S. Pat. No. 5,466,231 issued Nov. 14, 1995 adheres or laminates a layer or sheet of polyethylene to the large lateral surfaces of a polyvinyl acetal sponge and then perforates the polyethylene sheet to allow moisture transfer. The product works but the polyethylene skin cannot be compressed because it will delaminate. As a result, the product in the single compressed dimension is too large to permit comfortable insertion.

U.S. Pat. No. 5,370,656 inferentially discloses proving a fluid impervious silicone layer to a polyvinyl acetal "C" shaped throat pack sponge.

Materials that are closely related chemically to the polyvinyl acetate-alcohol-acetal porous bodies of this invention have been used in a variety of biologically related applications. The following uses of related materials is considered exemplary and illustrative of such uses. Tan, J. H.,; et al, (Radiation Research, vol. 124, no. 1, p. 43–9, October 1990) implanted a polyvinyl alcohol sponge disc in the subcutis of the thorax. A separating agent which includes a polyvinyl acetal resin having open cell structure and an average pore size of from about 10 to about 1000 micrometers has been described in U.S. Pat. No. 5,085,781 issued Feb. 4, 1992. U.S. Pat. No. 5,370,656 issued Dec. 6, 1994 describes a throat sponge which maybe pre-hydrated which is made from polyvinyl acetal that is fast working and expands instantly and uniformly to absorb 23 to 27 times its weight in fluids.

The present invention solves the above noted problems with wound care sponges in a manner not disclosed in the known prior art.

SUMMARY OF THE INVENTION

The present invention is directed toward a polyvinyl acetal wound care sponge with a smooth outer silicone skin bonded thereto, the skin having less porosity then the foam center and a low durometer. The PVA sponge is washed free of formaldehyde, dried and hydrated and a thin coating of low durometer silicone is applied to the surface of the sponge and heated at a low temperature over 8 to 16 hours to cure the silicone skin bonding it to the sponge increasing the tear strength of the skin while preserving elasticity. The cured skin has an elongation expansion ranging from about 200 to about 600% and increased tear strength. The composite wound dressing allows moisture adsorption through the silicone skin into the PVA sponge body but presents a smooth outer surface precluding wound growth into the sponge material.

It is an object of the invention to provide a wound care dressing having a slightly porous skin to allow for the passage of moisture into the sponge body.

It is another object of the invention to provide a wound care dressing having a skin of a different material from the body of the dressing which exhibits physical properties similar to the PVA sponge in elasticity and strength.

It is yet another object of the invention to provide a wound care dressing which is soft and flexible while exhibiting better fluid retention with less leakage than prior art wound care sponges.

It is still another object of the invention to provide a wound dressing which allows comfortable easy removal of the dressing from the wound and upon removal leaves the wound area clean with minimal tearing of the wound area.

In the accompanying drawings, there is shown an illustrative embodiment of the invention from which these and other objectives, novel features and advantages will be readily apparent.

DETAILED DESCRIPTION OF THE PREFERRED EMBODIMENT

Figure 1:
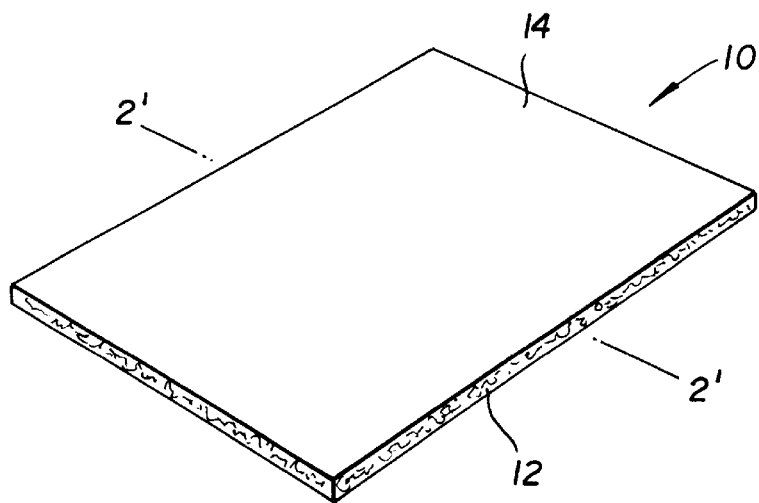
FIG. 1 is a perspective view of the inventive wound care dressing.
Figure 2:
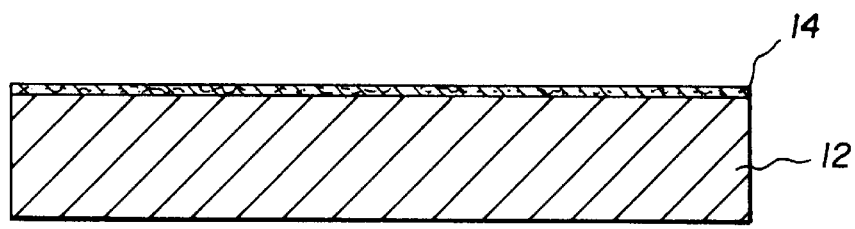
FIG. 2 is a cross sectional view of a inventive wound care dressing shown in FIG. 1 taken along lines 2'—2'.
Figure 3:
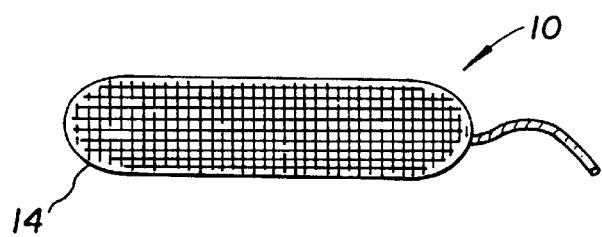
FIG. 3 is a perspective view of a wound care device with total silicone skin encapsulation.

The best mode and the preferred embodiment of the novel wound care dressing is shown generally in FIGS. 1 and 2.

FIG. 1 illustrates a wound care dressing or sponge 10 formed with an inner more porous polyvinyl acetal body 12 having an outer silicone skin 14. The outer skin 14 is a thin coating of low durometer silicone applied to a flat surface of the sponge, the coated flat surface in turn being adapted to be applied to the wound in the case of a wound dressing. The body and skin of the dressing is then heated to between 100° F. and 150° F. for between 8 to 16 hours which cures the silicone skin and bonds it to the sponge body 12. The bonded low durometer silicone skin preferably ranging from between about Shore A 10 to about Shore A 40 is less than 1 mm in thickness, ranging from 1 to 4 mils, preferably 2 mils in thickness and exhibits properties similar to the PVA sponge body in elasticity and strength while being slightly porous to allow for a minimal passage of moisture. The cured skin 14 has an elongation expansion ranging from 200 to 600%, preferably between 400 to 550% and increased tear strength as a result of the longer cure time. The silicone used in the invention is commercially available from GE Silicones under the product designation LIM6010.

The GE silicone product has a specific gravity of 1.05, a viscosity (cps) of about 30,000 and a Shore A Durometer ranging from 10 when molded at 30 seconds to 15 at one hour at 350° F. The silicone has an elongation depending upon molding time ranging from 510 to 440 and a tensile strength psi (Mpa) ranging from 400 (2.76) to 450 (3.10) and tear strength Die B lb/in (KN/M) of 32 (5.62) to 60 (10.51) depending upon the length of time of curing. It is believed that the durometer increases when baked at a lesser temperature for a greater time and that this curing causes both chemical and mechanical bonding between the PVA material and the silicone. If desired the sponge and silicone can be heated and quickly cured from 1 to 30 seconds at 300° F. and 450° F. to provide a skin with greatly reduced to no porosity. Polyvinyl acetal has been selected because of its absorbability of fluids, ability to be treated with microbial materials and because it can absorb shock through the flexible cell structure of the material while retaining rigidity allowing it to maintain shape when placed over a wound. The wound care sponge 10 wicks up fluid from the body wound while the skin prevents tissue growth into the sponge and ease of removal.

The base polyvinyl acetal material prior to treatment with the silicone skin is heated and solublized at 190 degrees Fahrenheit, mixed with a cross linking agent and catalyzed and placed on a sheet. After removing the sheet of PVA material it is washed with a di-water carrier several times to remove the forming formaldehyde so that the formaldehyde is undetectable (under 1 part per million) by high pressure liquid chromatography. The formaldehyde content is believed to be less than 0.1 part per million. The PVA material is dried and hydrated and then rung out to remove any excess moisture. A thin coating of low durometer silicone (less then 1 mm), preferably about 2 mils but within the range of 1–4 mils is then applied to at least one surface of the sponge by dipping the same in a silicone bath and scraping the surface the surface with a doctor blade. Alternatively, the sponge body may be coated with a spray by an air brush or by rolling the article with a fluidized bed coating technique. Spraying can be carried out with an air brush such as Badger Model 150 commercially available from Badger Air Brush Company. Once the silicone is coated on the PVA body surface, it is then heated to between 100° F. to about 150° F. for a period of between 8 to 16 hours curing the silicone skin and bonding it to the sponge body.

When a shaped product is desired, the base polyvinyl acetal material is heated and solublized at 190 degrees Fahrenheit, mixed with a cross linking agent and catalyzed and placed in a cast to obtain the desired form. After removing the molded product from the cast it is washed with a di-water carrier several times to remove the forming formaldehyde so that the formaldehyde is undetectable (under ½ part per million) by high pressure liquid chromatography. The formaldehyde content is believed to be less than 0.1 part per million. The material is dried and then hydrated and rung out to remove any excess moisture. The product is sprayed, brushed or dipped in silicone to form a layer less than 1 mm preferably about 2 mils but within a range of 14 mils and subsequently cured in a mold at 100° F. to about 150° F. for about 8 hours to about 16 hours to allow for intimate contact on one or more surfaces of the sponge. If an impervious layer of silicone skin is required on the product the product is covered with a thicker coat of silicone or cured at 1–30 seconds at a higher temperature of 300° F. to about 400° F. The manufactured article can be used for many purposes such as a wound dressing, nasal packing, posterior nasal packing or other suitable medical usages.

A thicker silicone coating can be applied from 1–3 mm in thickness to the outer surface of the sponge body to make the body moisture proof.

The formed product has a low durometer silicone skin of less than 1 mm in thickness preferably about 2 mils allowing the skin to exhibit properties similar to the PVA sponge body in elasticity ranging from 200 to 600% elongation and increased tear strength. The silicone skin is preferably about 2 mils thick allowing for a minimal passage of moisture. If desired the skin can be made thicker and cured faster to provide a moisture barrier. The PVA sponge body used in the product has an average pore size of 20 to 30 microns on the surface less than the pore size in the body and is a white open-celled sponge, instantaneous fluid wicking, with an absorptive capacity of up to 27 times it's weight in fluids and a retained fluid capacity of up to 16 times its own weight in fluids.

Any of a variety of substances can be introduced into the PVA after washing but before adding the silicone coating to remove undesired residue, e.g, by soaking or immersing the PVA in a solution of the desired substance(s) followed by drying of the PVA. This introduction occurs before soaking sponge material in the glycerine. Substances which can be readily incorporated in the PVA in this or any other suitable manner include antimicrobials and/or antibiotics such as erythomycin, bacitracin, neomycin, penicilin, polymyxin B, tetracycline viomycin, chloromycetin and streptomycins, cefazolin, ampicillin, tobramycin, clindamycine and gentamycin, etc.; amino acids, peptides, vitamins, inorganic elements, cofactors for protein synthesis; hormones; synthesizers; enzymes such as collagenase, peptidases, oxidases, etc.; angiogenic drugs and polymeric carriers containing such drugs; biocompatible surface active agents; antigenic agents. The amounts of optionally added substances can vary widely with optimum levels being readily determined in a specific case by routine experimentation. Another germicidal absorptive material which can be used in the present invention is disclosed in U.S. Pat. No. 5,811,471 issued Sep. 22, 1998. In this patent a polyvinyl acetal sponge is incubated in a solution of germicidal disinfectant dye which is binded to the sponge and allows the sponge to inhibit bacterial growth. It is also envisioned that the sterile albumin disclosed in U.S. Pat. No. 5,919,907 issued Jul. 6, 1999 can be used with the present invention. Another antimicrobial treatment is disclosed in U.S. Pat. No. 5,589,072 issued Dec. 31, 1996 and can be used with the present invention.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

What I claim is:

1. A wound dressing comprising a body made of polyvinyl acetal material with a central porous section and less porous outer skin and a smooth outer silicone skin bonded to at least one surface of the polyvinyl acetal body, said silicone outer skin having elasticity which approximates the elasticity of the polyvinyl acetal body, a low durometer and a thickness ranging between about 1 mil and about 0.0394 inches and being slightly porous to allow for passage of moisture into said polyvinyl acetal body while precluding tissue ingrowth.

2. A wound dressing as claimed in claim 1 wherein said wound dressing body polyvinyl acetal material has less than 1 part per million of formaldehyde residing in the body.

3. A as claimed in claim 1 wherein said outer silicone skin forms a surface which is adapted for placement against an open wound surface.

4. A wound dressing as claimed in claim 1 wherein said wound dressing body is impregnated with antimicrobials and/or antibiotics from the group consisting of erythomycin, bacitracin, neomycin, penicillin, polymyxin B, tetracycline, viomycin, chloromycetin and streptomycins, cefazolin, ampicillin, tobramycin, clindamycine and gentamycin.

5. A wound dressing as claimed in claim 1 wherein said wound dressing body is impregnated from the group consisting of amino acids, peptides, vitamins, inorganic elements, co-factors for protein synthesis.

6. A wound dressing as claimed in claim 1 wherein said wound dressing body is impregnated with antigenic agents.

7. A wound dressing as claimed in claim 1 wherein said silicone skin ranges from about 1 to about 4 mils in thickness.

8. A wound dressing as claimed in claim 1 wherein said silicone skin is about 2 mils thickness.

9. A wound dressing as claimed in claim 1 wherein said low durometer silicone ranges from about Shore A 10 to about Shore A 40.

10. A wound dressing as claimed in claim 1 wherein said silicone skin has an elongation ranging from 200% to 600%.

11. A wound dressing as claimed in claim 1 wherein said silicone skin has a tear strength Die B lb/in ranging from between about 30 to about 100.

12. A wound dressing sponge device comprising a body made of polyvinyl acetal material with a central porous section and less porous outer skin and a low durometer outer silicone skin bonded to at least one surface of the polyvinyl acetal body, said outer skin silicone having an elongation expansion ranging from about 200 to about 600%, a thickness of about 2 mils and being slightly porous to allow for passage of moisture into said polyvinyl acetal body, said silicone skin allowing three dimensional compression of the sponge body.

13. A wound dressing sponge device comprising a body made of polyvinyl acetal material with a central porous section having a substantially uniform pore size and less porous outer skin ranging from 1 micron to about 100 microns in thickness and a low durometer outer silicone skin bonded to the polyvinyl acetal body, said silicone skin having a low durometer of between Shore A 10 and Shore A 40 and an elasticity substantially the same as the polyvinyl acetal body, said outer silicone skin having a thickness ranging from about 0.05 mm to about 1 mm and an elongation ranging from about 400 to about 550% and being porous to allow for minimal passage of moisture into said polyvinyl acetal body while precluding tissue growth into the sponge body.

14. A wound dressing as claimed in claim 13 wherein said polyvinyl acetal material has less than 1 part per million of formaldehyde residing in the body.

15. A medical device comprising a body made of polyvinyl acetal with a central section with a reduction of the number of the mean sized occurring pores in the central portion to an outer skin of said polyvinyl acetal body being reduced from about 20% to about 30%, and a silicone skin bonded to said body, said silicone skin having an elongation range of about 200 to about 600% and being less than 1 mm thickness.

16. A medical device as claimed in claim 15 wherein said silicone skin is porous.

17. A medical device as claimed in claim 15 wherein said silicone skin is impervious.

18. A medical device comprising a shaped cast body made of polyvinyl acetal material having less than ½ part per million of formaldehyde residing in the body with a central porous section and less porous outer skin ranging from about 5 microns to about 60 microns in thickness surrounding at least a substantial portion of said central section, said outer skin having a reduction in the pore sizes from those occurring the central portion and a silicone layer having a low durometer ranging from about Shore A10 to about Shore A40 with an elongation range of about 400% to about 600% bonded to at least one outer skin surface of said shaped cast body.

19. A method of constructing a wound dressing comprising the steps of:
 a). formulating a PVA foam product;
 b). washing the formed PVA foam product;
 c). wringing out the formed PVA foam product to remove excess moisture;
 d). applying a coating of silicone ranging from about 0.0254 mm to about to 1 mm to the surface of the PVA foam product;
 e). heat treating the coated PVA foam product to bond the silicone to the PVA sponge body forming a skin less than 1 mm in thickness which exhibits properties similar to the PVA sponge in elasticity and strength.

20. A method of constructing a wound dressing as claimed in claim 19 wherein step d) wherein said coating is about 0.05 mm thickness.

21. A method of constructing a wound dressing as claimed in claim 19 wherein the application of step d) is dipping the product in a silicone bath.

22. A method of constructing a wound dressing as claimed in claim 19 wherein the application of step d) is by spraying at least one surface of the product with silicone.

23. A method of constructing a wound dressing as claimed in claim 19 wherein the application of step d) is by rolling silicone at least one surface of the product.

24. A method of constructing a wound dressing as claimed in claim 19 wherein step e) heat treating the coated PVA foam product is from about 8 to about 16 hours at about 100° F. to about 150° F.

25. A method of constructing a wound dressing comprising the steps of:
  a). formulating a PVA foam product;
  b). washing the formed PVA foam product to remove formaldehyde;
  c). wringing out the formed PVA foam product to remove excess moisture;
  d). applying a coating of silicone with a durometer having substantially the same elasticity and strength as the PVA foam product on which it is applied; and
  e). heat treating the coated PVA foam product in a range of 100° F. and 200° F. for a period of about 8 hours to about 16 hours to bond the silicone to the PVA sponge body forming a skin less than 1 mm in thickness which exhibit properties similar to the PVA sponge in elasticity and strength.

26. A wound dressing as claimed in claim 25 wherein said low durometer silicone ranges from about Shore A 10 to about Shore A 40.

27. A wound dressing as claimed in claim 25 wherein said silicone skin has an elongation ranging from 200% to 600%.

28. A method of constructing a wound dressing as claimed in claim 19 including the step of impregnating the PVA sponge product with antimicrobials and/or antibiotics from the group consisting of erythomycin, bacitracin, neomycin, penicillin, polyinyxin B, tetracycline, viomycin, chioromycetin and streptomycins, cet[]zolin, ampicillin, tobramycin, clindamycine and gentamycin.

* * * * *